(12) United States Patent
Kim et al.

(10) Patent No.: US 6,399,536 B2
(45) Date of Patent: Jun. 4, 2002

(54) HIGH PERFORMANCE CATALYST SYSTEMS FOR THE SYNTHESIS OF ALKYLENECARBONATES

(75) Inventors: Hoon Sik Kim; Byung Gwon Lee; Sang Deuk Lee; Young Soo Kwon; Hyun Joo Lee, all of Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/780,236

(22) Filed: Feb. 9, 2001

(30) Foreign Application Priority Data

Feb. 11, 2000 (KR) .............................. 00-6400

(51) Int. Cl.⁷ .......................... B01J 31/30; B01J 31/32; C07D 317/10; C07D 3/02
(52) U.S. Cl. .................. 502/169; 502/153; 549/229; 549/513; 546/9
(58) Field of Search ................ 502/153–169; 549/229, 513; 546/9

(56) References Cited

U.S. PATENT DOCUMENTS

| 4,233,221 A | * 11/1980 | Raines et al. | 549/230 |
| 4,344,881 A | 8/1982 | Strege et al. | 549/229 |
| 4,353,831 A | 10/1982 | Strege et al. | 549/229 |
| 5,144,066 A | * 9/1992 | Saitou et al. | 562/416 |
| 5,391,767 A | 2/1995 | Mais et al. | 549/229 |

FOREIGN PATENT DOCUMENTS

| JP | 59-013776 | 1/1984 | ......... C07D/317/36 |
| JP | 07-206846 | 8/1995 | ......... C07D/317/36 |
| JP | 07-206847 | 8/1995 | ......... C07D/317/36 |
| JP | 09-067365 | 3/1997 | ......... C07D/317/36 |
| JP | 09-235252 | 9/1997 | ........... C07C/69/96 |

OTHER PUBLICATIONS

U.S. application Ser. No. 09/780,235, filed Feb. 9, 2001.

* cited by examiner

Primary Examiner—Alan L. Rotman
Assistant Examiner—Rita Desai
(74) Attorney, Agent, or Firm—Darby & Darby

(57) ABSTRACT

A catalyst of the formula (1) for the synthesis of alkylene carbonate by reacting alkylene oxide and carbon dioxide $$L_mMX_n \qquad (1)$$

wherein L is selected from a group of pyridines;
M is a metal atom selected from Zn, Fe, Mn, Pb and In;
X is a halogen atom selected from Cl, Br and I;
m is 1 or 2, and
n is 2 or 3.

10 Claims, No Drawings

HIGH PERFORMANCE CATALYST SYSTEMS FOR THE SYNTHESIS OF ALKYLENECARBONATES

BACKGROUND OF THE INVENTION

1. Field of the Invention

The present invention relates to catalysts for the synthesis of alkylene carbonates by reacting alkylene oxide and carbon dioxide.

2. Description of the Background Art

Alkylene carbonates are used in polycarbonate synthesis, as a solvent for polymer electrolyte, an intermediate in pharmaceutical process, an oxyalkylation agent in dyestuff synthesis, a protectant in processing plant and a solvent in textile production process.

Alkylene carbonate has been prepared by reacting carbon dioxide and alkylene oxide in the presence of a catalyst, represented in Scheme 1.

Scheme 1

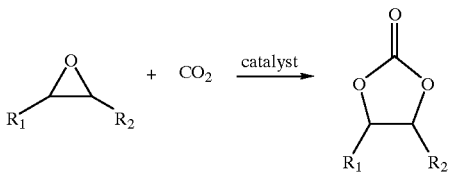

wherein, $R^1$ and $R^2$ are each independently H, $C_1$–$C_4$ alkyl or phenyl group.

In the above reaction, however, there is a limitation that alkylene oxide either decomposes or polymerizes at higher reaction temperatures.

Many catalysts have been developed including inorganic salts, phosphonium halide and ammonium halides. For instance, Japanese Laid-Open Patent No S59-13776 introduced a method of using tetraalkyl halide such as tributyl methyl phosphonium iodide as a catalyst. Japanese Laid-Open Patent No H9-67365 introduced a method of using KI as a catalyst and Japanese Laid-Open Patent No. H9-235252 describes a method of using polystyrene copolymer containing quaternary phosphonium groups.

These patents claim that the product yield is 50–95% when the reaction is performed at 100–170° C. for 1–5 hours. However, in order to achieve a high yield, longer reaction time and higher reaction temperature are required. Also the water content in the raw materials, carbon dioxide and alkylene oxide has to be reduced to a few hundred ppms.

Japanese Laid-Open Patent No. H7-206846 introduced a method of using an ion change resin substituted with the catalysts such as CsOH, RbOH and ammonium halides. In U.S. Pat. No. 4,233,221, a method of using DOWEX and Amberlite ion exchange resin was reported with a low yield of 30–80% at 80–100° C.

Besides the above-mentioned materials, a phthalocyanine complex containing Co, Cr, Fe, Mn, Ni, Ti, V, or Zr has been used as catalysts Also in Japanese Laid-Open Patent No. H7-206847, a catalyst system using a heteropolyacid whose hydrogen ion is substituted by Rubidium or Cesium was introduced These two cases, however, require expensive catalysts with low yield of 30–90% at relatively high reaction temperature of 120–180° C.

As mentioned above, the catalysts disclosed in the above arts have one or more problems in terms of activity, reaction condition, cost, water sensitivity, etc.

OBJECTS OF THE INVENTION

Therefore the object of the present invention is to provide catalysts for the synthesis of alkylene carbonates from alkylene oxide and carbon dioxide with a high yield and selectivity in a short reaction time under a mild reaction condition

SUMMARY OF THE INVENTION

The present invention provide a catalyst of the formula (1) for the synthesis of alkylene carbonate by reacting alkylene oxide and carbon dioxide $$L_mMX_n \qquad (1)$$

wherein L is selected from a group of pyridines;
M is a metal atom selected from Zn, Fe, Mn, Pb and In;
X is a halogen ayom selected from Cl, Br and I;
m is 1 or 2; and
n is 2 or 3.

In particular, the catalyst of the present invention is used to synthesize alkylene carbonate of the formula (2)

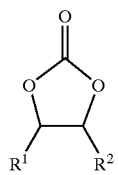

(2)

wherein $R^1$ and $R^2$ are each independently H, $C_1$–$C_4$ alkyl or phenyl.

The present invention also provide a method for synthesizing alkylene carbonate from alkylene oxide and carbon dioxide by using the catalyst of the formula (1)

DETAILED DESCRIPTION OF THE PREFERRED EMBODIMENTS

The present inventors have found that a catalyst $L_mMX_n$ is more effective than the conventional catalysts in preparing alkylene carbonate from alkylene oxide and carbon dioxide The pyridine ligand (L) in $L_mMX_n$ is labile enough and is easily displaced by the incoming alkylene oxide to give alkylene oxide coordinated species. The coordinated alkylene oxide is ring-opened by the attack of the displaced pyridine to give an active species The pyridine ligand (L) includes the compounds having the structures of the formulae (3), (4) and (5)

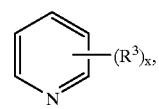

(3)

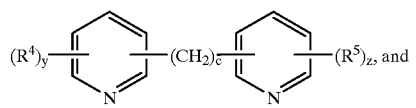

(4)

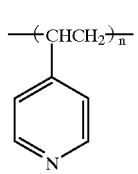
(5)

wherein $R^3$, $R^4$ and $R^5$ are each independently H, $C_1$–$C_4$ alkyl or phenyl, each of x, y and z is independently an integer from 0 to 3; and c is an integer from 2 to 4.

In the formula (1), MX may be a compound selected from the group consisting of $ZnX_2$, $FeX_2$, $FeX_3$, $MnX_2$, $PbX_2$, and $InX_3$.

The amount of the catalyst for the synthesis of alkylene carbonate is preferably 0.005~0.1 mole per mole of alkylene oxide. In case the amount of the catalyst used is less than 0.005 mole, reaction becomes too slow And in case the amount of the catalyst is more than 0.1 mole, the reaction rate and yield do not improve any further. The reaction pressure of the present invention could be 10~100 atm.

Since the reaction is not greatly influenced by the presence of nitrogen hydrogen, hydrocarbons and small amounts of water in carbon dioxide and alkylene oxide, it is possible to use commercially available carbon dioxide and alkylene oxide without further purification step.

Considering the equipment and operating cost, it is preferable to operate a reaction at a pressure of 10–100 atm.

The reaction temperature is preferabley 60–140° C. The reaction proceeds too slow at temperatures lower than 60° C. When the reaction temperature is too high, alkylene oxide either decomposes or undergoes a self-polymerization reaction.

Although the above reaction could be performed in the absence of the solvent, it is possible to use solvent to prevent excess heat production during the reaction. It is preferable to use alkylene carbonate that is produced from the raw material alkylene oxide as a solvent. For instance, ethylene carbonate is a preferable solvent when ethylene carbonate is synthesized from ethylene oxide, and propylene carbonate is preferable when propylene carbonate is synthesized from propylene oxide The reaction could be performed by a batch process using the reactor provided with a stirrer or by a continuous process using a bubble column The invention will be further illustrated by the following examples, but not limited to the examples given.

EXAMPLE 1

The catalysts of the present invention were synthesized by using the following method.

Preparation of $(C_5H_5N)_2ZnBr_2$: In a 250 ml flask 100 ml of tetrahydrofurane, $ZnBr_2$ (2.0 g, 8.9 mmol), pyridine (1.4 g, 17.8 mmol) were added and reacted for an hour. After the reaction, the precipitate was collected by filtration and dried under a vacuum to give 3.3 g of $(C_5H_5N)_2ZnBr_2$.

EXAMPLE 2

A 200 ml high pressure reactor was loaded with ethylene oxide (16.80 g, 380 mmol) and $(C_5H_5N)_2ZnBr_2$ (383 mg, 1.0 mmol) and pressurized with 10 atm of carbon dioxide. After increasing the temperature to 100° C., carbon dioxide was introduced again to increase the pressure to 30 atm. During the course of reaction, carbon dioxide was continuously supplied from a reservoir tank to maintain the pressure at 30 atm.

After the reaction at 100° C. for 1 hour, the reactor was cooled to room temperature. Volatiles were removed and the solid product was separated and weighed to be 31.5 g. The yield analyzed was 93.8% by gas-liquid chromatography and mass analysis.

EXAMPLES 3~9

The process of Example 2 was repeated by the metal (M) and halogen atoms (X) in $L_mMX_n$. The results are shown in Table 1

TABLE 1

| Example | Metal halide compound | Product weight (g) | Yield (%) |
|---|---|---|---|
| 3 | $(C_5H_5N)_2ZnCl_2$ | 20.4 | 60.7 |
| 4 | $(C_5H_5N)_2ZnI_2$ | 27.0 | 95.8 |
| 5 | $(C_5H_5N)_2FeBr_2$ | 26.5 | 78.9 |
| 6 | $(C_5H_5N)_2FeBr_3$ | 27.0 | 80.3 |
| 7 | $(C_5H_5N)_2PbI_2$ | 23.7 | 70.5 |
| 8 | $(C_5H_5N)_2MnBr_2$ | 26.7 | 79.5 |
| 9 | $(C_5H_5N)_2InCl_3$ | 24.6 | 73.1 |

EXAMPLES 10~17

The process of Example 2 was repeated by varying pyridine ligands (L) in $L_mZnBr_2$. The results are shown in Table 2.

TABLE 2

| Example | Pyridine ligand (L) | Product weight (g) | Yield (%) |
|---|---|---|---|
| 10 | 2-methyl pyridine | 32.2 | 95.8 |
| 11 | 2-ethyl pyridine | 32.3 | 96.2 |
| 12 | 2-propyl pyridine | 31.2 | 93.0 |
| 13 | 2-n-butyl pyridine | 30.3 | 90.1 |
| 14 | 2-phenyl pyridine | 30.1 | 89.5 |
| 15 | 1,2-bis(4-pyridyl) ethane | 31.6 | 94.1 |
| 16 | 1,2-bis(2-pyridyl) ethane | 30.5 | 90.7 |
| 17 | Polyvinylpyridine | 31.3 | 93.1 |

EXAMPLES 18~21

The reactions were performed under the identical conditions as in Example 2 except the reaction temperature was varied in the range 60–120° C. The results are shown in Table 3.

TABLE 3

| Example | Reaction Temperature (° C.) | Product weight (g) | Yield (%) |
|---|---|---|---|
| 18 | 60 | 12.0 | 35.7 |
| 19 | 80 | 29.6 | 88.1 |
| 20 | 100 | 31.5 | 93.6 |
| 21 | 120 | 31.9 | 95.1 |

EXAMPLE 22~24

The reaction was performed under the identical condition as in Example 2 except that the reaction pressure was varied in the range 20–100 atm. The results are shown in Table 4.

TABLE 4

| Example | Reaction Pressure (atm) | Product weight (g) | Yield (%) |
|---|---|---|---|
| 22 | 20 | 30.9 | 91.9 |
| 23 | 50 | 31.5 | 93.8 |
| 24 | 100 | 32.0 | 95.3 |

EXAMPLES 25~28

The reaction were performed under the identical condition as in Example 2 except that the molar ratio of $(C_5H_5N)_2ZnBr_2$ to ethylene oxide was varied in the range of 0.0005–0.1%. The amount of ethylene oxide was fixed at 16.80 g (380 mmole) The results are shown in Table 5.

TABLE 5

| Example | Catalyst/ethylene oxide (molar ratio) | Product weight (g) | Yield (%) |
|---|---|---|---|
| 25 | 0.0005 | 20.2 | 60.1 |
| 26 | 0.001 | 31.0 | 93.8 |
| 27 | 0.01 | 32.9 | 98.1 |
| 28 | 0.1 | 33.1 | 98.5 |

EXAMPLE 29~32

The reactions were performed under the identical condition as in Example 2 except that different alkylene oxides was employed. The results are shown in Table 6.

TABLE 6

| Example | Alkylene oxide | Product weight (g) | Yield (%) |
|---|---|---|---|
| 29 | Propylene oxide | 38.0 | 98.0 |
| 30 | 2-methyl-1,2-epoxy propane | 40.5 | 91.1 |
| 31 | 2,3-epoxy butane | 39.4 | 88.6 |
| 32 | Styrene oxide | 61.0 | 97.8 |

EXAMPLE 32~33

The reaction were performed under the identical condition as in Example 2 except that ethylene carbonate or propylene carbonate was used as a solvent. The amount of the solvent used was 200% of ethylene oxide by weight The results are shown in Table 7.

TABLE 7

| Example | Solvent | Product weight (g) | Yield (%) |
|---|---|---|---|
| 32 | Ethylene carbonate | 31.5 | 93.8 |
| 33 | Propylene carbonate | 31.5 | 93.8 |

According to the present invention, alkylene carbonates can be produced in high yield at relatively low temperature and pressure by using the catalyst of the formula (1). The catalyst of the present invention has several advantages in terms of economical point of view because it is inexpensive, highly active and reusable.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the meets and bounds of the claims, or equivalence of such meets and bounds are therefore intended to be embraced by the appended claims.

What is claimed is:

1. A catalyst of the formula (1) for the synthesis of alkylene carbonate by reacting alkylene oxide and carbon dioxide, said catalyst having the structure:

$$L_mMX_n$$

wherein L is selected from a group of formula (3) and (4)

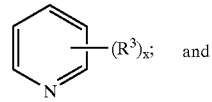

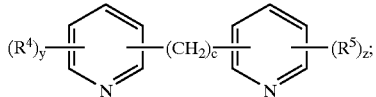

wherein $R^3$, $R^4$ and $R^5$ are each independently $C_{2-4}$ alkyl or phenyl; each of x, y and z is independently 1, 2 or 3; and c is an integer from 2 to 4;

M is a metal atom selected from Zn, Fe, Mn, Pb and In;

X is a halogen atom selected from Cl, Br and I;

m is 1 or 2; and n is 2 or 3.

2. The catalyst of claim 1 wherein said alkylene carbonate has a structure of the formula (2)

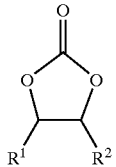

wherein $R^1$ and $R^2$ are each independently H, $C_1$–$C_4$ alkyl or phenyl.

3. The catalyst of claim 1 wherein MX in the formula (1) is a compound selected from the group consisting of $ZnX_2$, $FeX_2$, $FeX_3$, $MnX_2$, $PbX_2$ and $InX_3$.

4. A method for synthesizing alkylene carbonate from alkylene oxide and carbon dioxide by using any catalyst according to claims 1 or 2.

5. The method according to claim 4 wherein the molar ratio of the catalyst to alkylene oxide is in the range 0.0005~0.1:1.

6. The method according to claim 4, wherein the reaction is in the range 60–140° C.

7. The method according to claim 4 wherein the reaction pressure is in the range of 10–100 atm.

8. The method according to claim 4 wherein the reaction is carried out in the absence of a solvent.

9. The method according to claim 4, wherein alkylene carbonate is used as a solvent.

10. The method according to claim 9 wherein the solvent is selected from ethylene carbonate and propylene carbonate.

* * * * *